(12) United States Patent
Mendoza

(10) Patent No.: US 8,591,963 B2
(45) Date of Patent: Nov. 26, 2013

(54) DIRECT APPLICATION PET ODOR ELIMINATOR

(71) Applicant: Jose Luis Mendoza, San Diego, CA (US)

(72) Inventor: Jose Luis Mendoza, San Diego, CA (US)

( * ) Notice: Subject to any disclaimer, the term of this patent is extended or adjusted under 35 U.S.C. 154(b) by 0 days.

(21) Appl. No.: 13/645,597

(22) Filed: Oct. 5, 2012

(65) Prior Publication Data
US 2013/0089630 A1  Apr. 11, 2013

Related U.S. Application Data

(60) Provisional application No. 61/543,849, filed on Oct. 6, 2011.

(51) Int. Cl.
*A01N 65/00* (2009.01)

(52) U.S. Cl.
USPC .......................................... 424/725

(58) Field of Classification Search
None
See application file for complete search history.

(56) References Cited

U.S. PATENT DOCUMENTS

2013/0029884 A1*  1/2013  Malchesky et al. ........... 507/219

* cited by examiner

*Primary Examiner* — Michael Meller
(74) *Attorney, Agent, or Firm* — Sinorica, LLC

(57) ABSTRACT

A pet odor eliminator solution includes a concentrated mixture, water for diluting purpose, and organic orange extract. The concentrated mixture includes para chloro meta xylenol (PCMX), isopropanol, potassium ricolineate, terpineol, and water for mixing purpose. One part of the concentrated mixture is mixed with 299 parts of the water for diluting purpose and then 0.05 milliliters of the organic orange extract is added to a gallon of the concentrated mixture and the water for diluting purpose. The pet odor eliminator solution is a nontoxic solution which is used on pets to eliminate odor sources and to sanitize skin and fur areas.

1 Claim, 1 Drawing Sheet

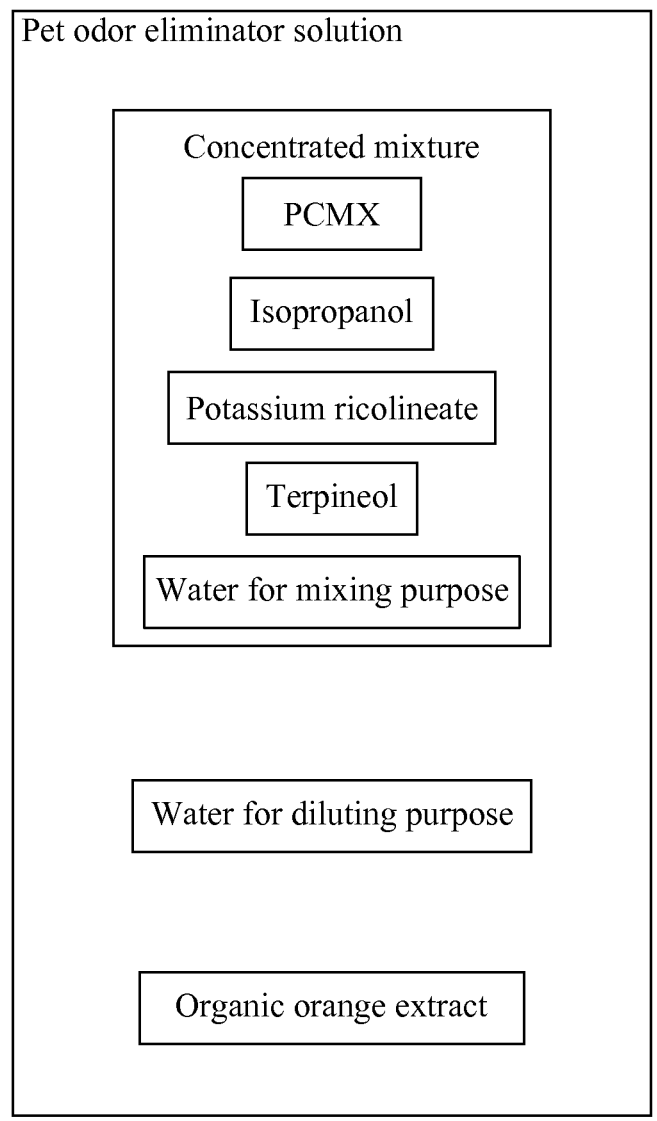

DIRECT APPLICATION PET ODOR ELIMINATOR

The current application claims a priority to the U.S. Provisional Patent application Ser. No. 61/543,849 filed on Oct. 06, 2011.

FIELD OF THE INVENTION

The present invention relates generally to a formula for reducing odors. More specifically, the formula can be applied directly to the pet's skin or the pet's fur to eliminate the pet odor sources.

BACKGROUND OF THE INVENTION

Para chloro meta xylenol (PCMX) is a broad spectrum antimicrobial that is effective against bacteria, such as both gram positive and gram negative, and fungi such as yeasts and molds. Currently, PCMX is used for a wide range of applications including
- as antiseptics in hospitals and medical practice
- as surgical hand scrub operations
- for the sterilization of instruments
- a low toxicity of PCMX has led to its wide use in the home, office and factory
- as an antiseptic skin wound cleaning and protectant formulations (liquids, creams, lotions)
- for industrial use as preventive micro-bacterial growth retardant
- as a general disinfectant and combined detergent/disinfectants In spite of this wide range of uses, PCMX has not been used to eliminate odors in a non-irritating formulation. It is therefore an object of the present invention to provide a formula that is non-irritating to the skin or eyes but retains the bactericidal-effectiveness of PCMX and eliminates odors, including but not limited to pet body and fur odors. The present invention provides a diluted formula that may be applied directly to the source of the odor, such as the pet's fur or skin.

BRIEF DESCRIPTION OF THE DRAWINGS

FIG. 1 is view of the system for pet odor eliminator solution.

DETAIL DESCRIPTIONS OF THE INVENTION

All illustrations of the drawings are for the purpose of describing selected versions of the present invention and are not intended to limit the scope of the present invention.

In reference to FIG. 1, the present invention is a formula for reducing or eliminating an odor while retaining antibacterial effectiveness, where the present invention comprises a concentrated mixture, water for diluting purpose, and organic orange extract. The present invention can be used on any places or surfaces such as homes, cars, furniture, toys, pets, and any other place or surface that needs to be deodorized and sanitized. The preferred embodiment of the present invention is used to reduce the pet's body or fur odor and disinfect specific bacteria, fungi, and viruses form the pets so that owners can have a peace of mind about the well-being of their pets.

The concentrated mixture comprises para chloro meta xylenol (PCMX), isopropanol, potassium ricolineate, terpineol, and water for mixing purpose. In the preferred embodiment, the concentrated mixture comprises 5% volume of the PCMX. The PCMX is an active ingredient of the present invention, where the PCMX is extremely effective against gram-positive bacteria, gram-negative bacteria, yeasts, molds, viruses, and a wide range of other microorganisms. The PCMX is a bactericidal that has a low degree of human toxicity with a broad spectrum of antimicrobial activities. The PCMX retains its bactericidal effectiveness in public domain for many years where the PCMX is used in antibacterial soaps and antiseptics. Additionally, the PCMX in the present invention takes a step forward by eliminating or reducing different odors from the source. The PCMX is formed as crystals or crystalline powder with white or cream color, where the PCMX comprises characteristic odor and melting point of 114-116° C. The PCMX is identified with the chemical abstract service (CAS) registry number 88-04-0 and also recognized with following synonyms.
1. 4 chloro 3, 5-dimethyl phenol
2. 4 chloro 3, 5 xylenol
3. 4 chloro meta xylenol
4. Chloroxylenol In the preferred embodiment, the concentrated mixture comprises 10% volume of the isopropanol where the isopropanol is mainly used for disinfecting purposes. The isopropanol is commonly known as rubbing alcohol and comprises colorless, flammable chemical compounds with a strong odor. The isopropanol is identified with the CAS registry number 67-63-0. In the preferred embodiment, the concentrated mixture comprises 6% volume of the potassium ricolineate and 10% volume of the terpineol. The terpineol is a naturally occurring alcohol and a slightly viscous clear liquid. The terpineol includes a pleasant odor similar to lilac and extracted from a plurality of natural sources. The terpineol can also be manufactured from the more readily available organic compounds. The present invention is able to use both naturally occurring terpineol and manufactured terpineol without comprising the functionality. The terpineol is identified with the CAS registry number 98-55-5. The potassium ricolineate functions as a stabilizing agent where the potassium ricolineate allows the PCMX, the isopropanol, and the terpineol to conduct their functionality within the present invention. The potassium ricolineate is identified with the CAS registry number 7492-30-0 and may also be known as the potassium ricinoleate. In the preferred embodiment, the concentrated mixture comprises 69% volume of the water for mixing purpose. The water for mixing purpose allows the PCMX, the isopropanol, the potassium ricolineate, and the terpineol to properly mixed together so that the concentrated mixture can be obtained.

In order for the concentrated mixture to be used on the humans or pets, the concentrated mixture is diluted with water for diluting purpose and the organic orange extract. The concentrated mixture is diluted with 1:300 ratios, where 1 part of the concentrated mixture is thoroughly mixed with 299 parts of the water for diluting purpose. Then 0.05 milliliters of the organic orange extract is added to a combined gallon of the concentrated mixture and the water for diluting purpose. The organic orange extract, which is filled with antioxidants like vitamin A and vitamin C, increases bacterial effectiveness and reduces the strong odor of the isopropanol. Since the organic orange extract does not contain synthetic chemicals or genetic engineering modifications, the organic orange extract also helps to prevent possible chemical toxicity of the present invention.

Since the concentrated mixture is diluted with the water for diluting purpose and the organic orange extract, a user can directly spray the present invention onto the pets so that the present invention can immediately eliminate all germs, bacteria, and fungi that generated pet odor. The user can simply rub the present invention into a pet's fur or brush into reach the skin until the present invention reaches the smelly fungus. Then a paper towel is sprayed with the present invention, and the paper towel is used to eliminate facial odors and clean hard to reach areas such as ears by the user. The user can use the present invention on dry fur or wet fur dog without any limitations. When the present invention is used on the pets, the PCMX and the isopropanol disinfect the skin and the fur. Additionally, the terpineol and the organic orange extract provide fresh and clean scent within the fur and the skin of the pets. The organic orange extract also fights to free radicals in the pet's body so that healthy skin can be developed. The users can use the present invention on their pets as many times as they desired, and the present invention provides zero side effects to the users or the pets.

The present invention retains all of the antibacterial effectiveness from the concentrated mixture. The present invention effectively fights against the following organisms upon direct contact. *Candida albicans* is a fungus/yeast, and a common microorganism that lives in humans and dogs which cause skin irritation and redness. Escherichia coli is a gram negative bacterium that is commonly found in the lower intestine of warm-blooded organism which can cause diarrhea. *Pseudomonas aeruginosa* is a free-living bacterium that can lead to ear, eye, and skin irritation. *Staphylococcus aureus* is a bacterial species that can cause a plurality of skin illnesses and staph infections. When the present invention is tested against *Candida albicans, Escherichia coli, Pseudomonas aeruginosa*, and *Staphylococcus aureus*, the present invention responds with a kill rate effectiveness of 99.9% within 30 seconds of contact. The present invention can also eliminate many other organisms with different kill rate effectiveness.

The present invention also meets all of the necessary standards with regarding to the deodorizing compositions. Additionally, the present invention is non-toxic and non-irritating solution. The present invention causes zero irritation to intact skin and broken skin of the pets and the humans and eyes of the pets and the humans.

Although the invention has been explained in relation to its preferred embodiment, it is to be understood that many other possible modifications and variations can be made without departing from the spirit and scope of the invention as hereinafter claimed.

What is claimed is:

1. A pet odor eliminator solution consisting essentially of a concentrated mixture of about 5 wt. % para chloro meta xylenol, about 10 wt. % isopropanol, about 6 wt. % potassium ricolineate, about 10 wt. % terpineol, about 69 wt. % water; and wherein one part of the concentrated mixture is mixed with 299 parts of water to form a water mixture and then 0.05 ml of an organic orange extract is added to one gallon of the water mixture to form said pet odor eliminator solution.

* * * * *